United States Patent [19]

Monticello

[11] Patent Number: 5,458,876
[45] Date of Patent: Oct. 17, 1995

US005458876A

[54] CONTROL OF MICROBIAL GROWTH WITH LANTIBIOTIC/LYSOZYME FORMULATIONS

[75] Inventor: Daniel J. Monticello, Elkhart, Ind.

[73] Assignee: Haarman & Reimer Corp., Elkhart, Ind.

[21] Appl. No.: 522,088

[22] Filed: May 14, 1990

Related U.S. Application Data

[63] Continuation-in-part of Ser. No. 434,671, Nov. 16, 1989, abandoned, which is a continuation-in-part of Ser. No. 287,719, Dec. 21, 1988, abandoned.

[51] Int. Cl.$^6$ .................................................. A61K 38/47
[52] U.S. Cl. .................... 424/94.61; 435/206; 426/61; 426/335; 426/532; 514/2; 514/21
[58] Field of Search ............................... 435/206; 426/61, 426/335, 532; 424/93, 94.61; 530/324; 514/2, 21

[56] References Cited

U.S. PATENT DOCUMENTS 4,740,593  4/1988  Gonzalez et al. ...................... 435/243

OTHER PUBLICATIONS

Mohamed et al., Chem Abstr. 102:128645f (1985).
Hnghey et al., Appl. Environ. Microbiol. 53:2165–2170 (1987).

Primary Examiner—Marian C. Knode
Assistant Examiner—Jean C. Witz
Attorney, Agent, or Firm—Jerome L. Jeffers

[57] ABSTRACT

Disclosed is a method of inhibiting procaryotic microbial growth which method involves adding a synergistically effective combination of a lantibiotic and lysozyme to an environment in which such microbial growth is to be inhibited.

16 Claims, 3 Drawing Sheets

CONTROL OF MICROBIAL GROWTH WITH LANTIBIOTIC/LYSOZYME FORMULATIONS

This application is a Continuation-In-Part of application Ser. No. 434,671 filed Nov. 16, 1989, now abandoned, which in turn is a Continuation-In-Part of application Ser. No. 287,719, filed Dec. 21, 1988.

BACKGROUND OF THE INVENTION

Nisin, a member of the group of bacteriocins known as lantibiotics, is an antimicrobial polypeptide produced by certain strains of *Lactococcus lactis* (formerly *Streptococcus lactis*). It is manufactured through the pure-culture fermentation of these bacteria with subsequent purification and drying. The first reported use of nisin as a food preservative occurred in 1951 when it was used to control the growth of *Clostridium butyricum* and *C. tyrobutyricum* in cheese (Hirsch et al, 1951, J. Dairy Research 18:205–206).

The term "lantibiotics" was coined by Schnell et al. (1988. Nature 333:276–278) to describe a group of bacteriocins including nisin which contain the amino acid lanthionine and other "non-protein" amino acids. The common properties of these bacteriocins are reviewed by Kellner et al. (1988. Eur. J. Biochem 177:53–59) wherein they note that there ". . . polycyclic polypeptide antibiotics possess a high content of unsaturated amino acids (dehydroalanine,m dehydrobutrine) and thioether amino acids (meso-lanthionine, (2S,3S,6R)-3-methyllanthionine). Furthermore, lysinoalanine, 3-hydroxyaspartic acid and S-(2-aminovinyl)-D-cystine [are] found in some members." Members of this group include nisin, subtilin, pep 5, epidermin, gallidermin, cinnamycin, Ro09-0198, duramycin and ancovenin. These ribosomally synthesized peptide antibiotics contain from 19 to 34 amino acids and are produced by various microbes including Staphlococcus species, Bacillus species and Streptomyces species. In addition to their unique composition of non-protein amino acids, they can be distinguished from other polypeptide antibiotics on the basis of their specificity. Bacteriocins in general, and the lantibiotics in particular, are characterized by a very narrow spectrum of action. Thus, only a few species of bacteria are sensitive to a particular bacteriocin at practical concentrations. This is in contrast with other broad spectrum polypeptide antibiotics, such as polymixin $B_1$ which are active against most bacteria and the "lytic peptides" discussed by Jaynes et al., in published international application wo 89/00194, which are active against most bacteria, yeasts and even mammalian cells.

Nisin occasionally occurs as a dimer with a molecular weight of about 7000. It contains several unusual amino acids including β-methyllanthionine, dehydroalanine, and lanthionine among its total of 34 amino acids. There are five unusual thio-ether linkages in the peptide which contribute to its stability in acid solutions. Nisin is one of the most thoroughly characterized bacteriocins, and shares remarkable homology of structure and action with other lantibiotics, for example Subtilin and epidermin [Buchman et al 1988. J. Bio. Chem. 263 (31):16260–16266]. Recent reviews of nisin, its physical properties and uses include "Bacteriocins of Lactic Acid Bacteria", T. R. Klaenhammer, 1988. Biochimie 70:337–349, "Nisin", A. Hurst, 1981. Avd. Appl. Microbiol. 27:85–121, and U.S. Pat. No. 4,740,593. Nisin is the collective name describing several closely related substances which exhibit similar amino acid compositions, and some limited range of antibiotic activity. This phenomenon is discussed by E. Lipinska in "Antibiotics and Antibiosis in Agriculture" (M. Woodbine, Ed.) Pp. 103–130.

The use of nisin to combat *L. monocytogenes* has been reported by M. Doyle; "Effect of Environmental and Processing Conditions on *Listeria Monocytogenes*", Food Technology, 1988.42(4):169–171. This reference describes the initial inhibition of the organism's growth (for about 12 hours) and reports that *L. monocytogenes* may grow at a pH level as low as 5.0 and is resistant to alkaline pH with the ability to grow at pH 9.6.

Lysozymes (Muramidase; mucopeptide N-acetylmucamoylhydrolase; 1,4-β-N acetylhexosaminodase, E.C. 3.2.1.17) are mucolytic enzymes which have been isolated from various sources and are well characterized enzymes. First discovered in 1922 by W. Fleming, egg white lysozyme was among the first proteins sequenced, the first for which a three dimensional structure was suggested using x-ray crystallography and the first for which a detailed mechanism of action was proposed. Its antimicrobial activity against gram positive bacteria is well documented, for example by V. N. Procter et al in CRC Crit. Reviews in Food Science and Nutrition, 1988, 26(4):359–395. The molecular weight of egg white lysozyme is approximately 14,300 to 14,600, the isoelectric point is pH 10.5–10.7. It is composed of 129 amino acids which are interconnected by four disulfide bridges. Similar enzymes have been isolated and characterized from other sources including such diverse producers as *Escherichia coli* bacteriophage T4 and human tears. Despite slight differences (for example, the human lysozyme has 130 amino acids) the capacity for hydrolysis of acetylhexosamine polymers remains essentially the same. Accordingly, for purposes of this invention, the term lysozyme is intended to include those cell wall degrading enzymes which have the ability to hydrolyze acetylhexosamine and related polymers.

Lysozyme is known to kill or inhibit the growth of bacteria and fungi, and is used in Europe to control the growth of the spoilage organism *Clostridium tyrobutyrucum* is cheese. It has also been proposed for use in a variety of other food preservation applications and has been reported to inhibit the growth of (and in some cases kill) *Listeria monocytogenes* (Hughey et al, 1987, Appl. Environ. Microbiol 53:2165–2170).

Published Australian patent application AU-A-18604/88 discloses the use of bacterialyzing enzyme products with N-acetylmuramidase, e.g. lysozyme, together with non-enzymatic preservatives for preserving foodstuffs. Non-enzymatic preservatives mentioned in this publication are complexing agents such as citric acid and EDTA, amino acids, particularly proteinogenic acids, such as cysteine, alanine, tyrosine and glycine and nucleosides and nucleotides such as inosine 5'-inosine monophosphate or phosphates such as tetrasodiumpyrophosphate (diphosphate), sodium tripolyphosphate (triphosphate) and polyphosphate or reddening agents such as alkali metal nitrates.

Lysozyme has been used for many years to prepare protoplasts of gram negative and gram positive bacteria to study cell membrane structure, function and interactions with various compounds. The mechanism of action of nisin was explored using protoplasts by Henning et al. (1986. International J. of Food Microbiology 3:121–134). They prepared protoplasts of *Micrococcus luteus* in an osmotically stabilized medium, and compared the action of nisin on these cells to the naturally occurring, cell wall deficient bacteria ("L-forms") of *Proteus mirablis*. Untreated cells, the protoplasts and L-forms were shown to be susceptible to nisin, demonstrating that the cell wall was not the target for nisin activity. There was no indication that lysozyme treated cells were more sensitive to nisin.

Jaynes et al., supra, describe the synergistic combination of "lytic peptides" from insect hemolymph and lysozyme for the lysis of mammalian cells infected with eucaryotic and procaryotic parasites and mention that the combination is also effective against bacteria.

In recently published international application WO89/12399 there is described a method whereby gram negative bacteria are controlled by a lanthionine containing bacteriocin in combination with a chelating agent and/or a detergent.

Recombinant DNA, protein engineering and chemical modification technologies can be used to effect subtle modifications of peptides and proteins to alter certain aspects of the molecules and to allow expression in new hosts. For example, the expression of nisin in new hosts is described in U.S. Pat. No. 4,740,593, and the genes for T4, human and egg white lysozyme as well as nisin and other "lantiotics" have been cloned. Human lysozyme has been expressed in *Bacillus subtilus* and *Saccharomyces cerevisiae*. These homologous molecules (nisin, epidermin, subtilin, etc. and T4, human and egg white lysozyme) should be considered as synonymous with nisin and lysozyme in the context of the present invention. It should not be necessary to use the pure components to achieve the synergistic effect. For example the combination of raw egg whites and nisin fermentation broth should exhibit synergistic anti-bacterial properties.

While nisin and lysozyme have been shown to individually inhibit the growth of some bacteria, it is not clear that either lysozyme or nisin by themselves can sufficiently inhibit the growth of these microorganisms when applied in economically feasible concentrations.

SUMMARY OF THE INVENTION

Figure 1:
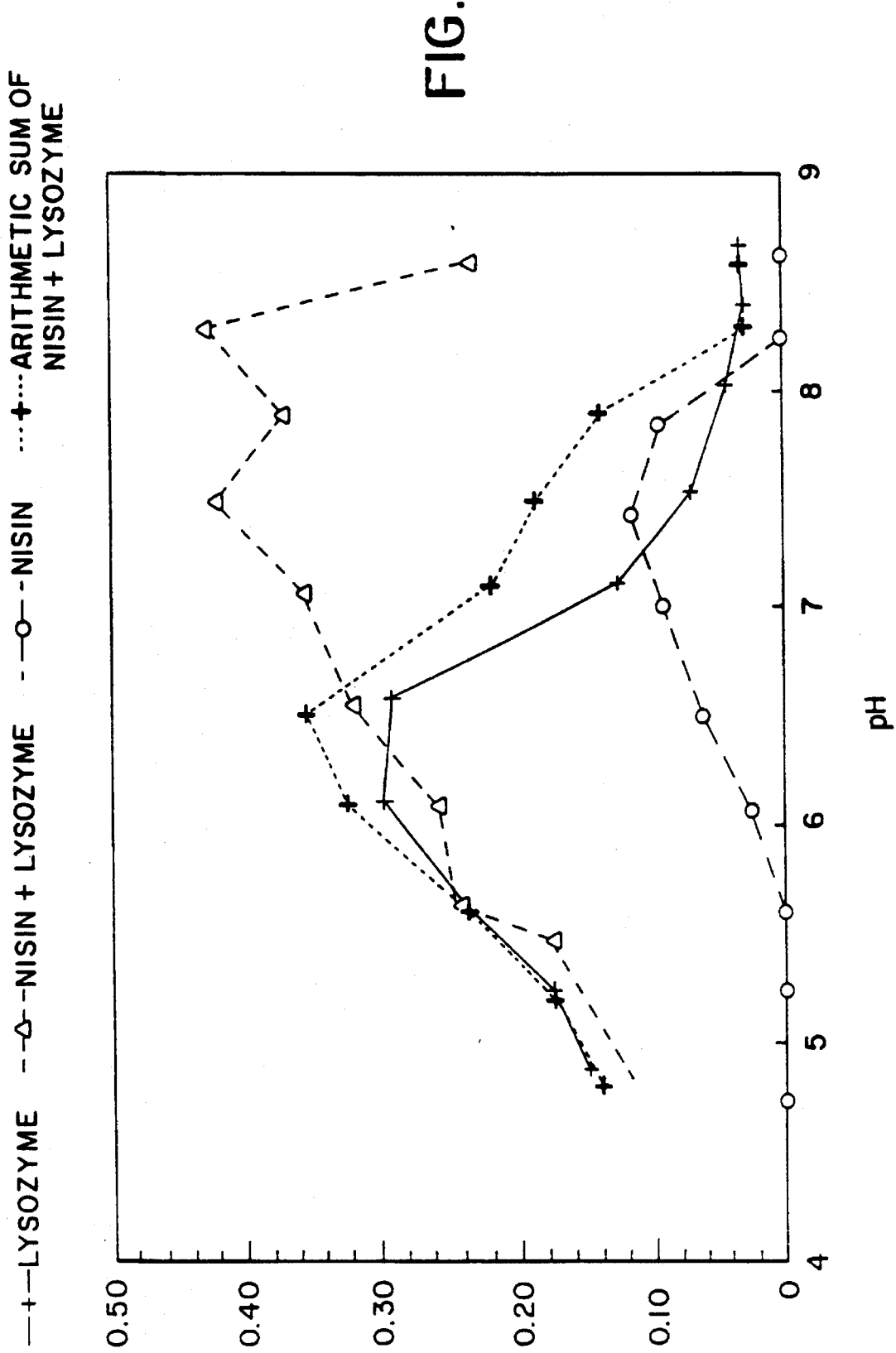
FIG. 1 is a graphical representation of lysis of *Listeria monocytogenes* by a combination of lysozyme and nisin as a function of pH.

The present invention is a method of controlling undesirable procaryotic microorganisms in an environment amenable to their growth which comprises adding to such environment a synergistically effective combination of a lantibiotic and lysozyme in an amount and under conditions sufficient for control of the bacteria.

The synergistic combination has exhibited the ability to inhibit the growth of gram negative and/or gram positive bacteria in some cases. In other situations the combination is lethal to the bacteria.

DESCRIPTION OF THE INVENTION

The present invention relates to the observation that one or more lantibiotic and lysozyme, in combination, can be used at significantly lower concentrations than either component alone to yield a similar degree of control of procaryotic microorganisms. Nisin, the best known lantibiotic, and lysozyme have been used separately in a variety of food preservation applications, e.g. they have been used individually to control pathogenic organisms such as *Clostridium botulinum* and spoilage organisms such as *C. tyrobutyricum* in dairy products, processed meats, sea foods, fresh and processed vegetables, seafood products, vegetable and fruit juices and beverages (both soft drinks and alcoholic). These food groups and beverages are exemplary of consumables that can be treated with the synergistic combination of the present invention. However, the cost of these substances has hindered the commercial acceptance of these applications. The antimicrobial properties of nisin and lysozyme are also useful in non-food applications including the control of certain infections in humans and animals, the control of microbial growth in chemical feedstocks and industrial products and in cleaning applications such as decontamination of surfaces having microbial contamination.

A variety of microorganisms have been reported to be affected by nisin or lysozyme. For nisin these are primarily gram positive bacteria including some species of Clostridia, Bacilli, Lactococci, Staphlococci, Pediococci, Micrococci, Microbacteria, and Lactobacilli generea, although published PCT application WO 8912399 discusses the activity of lanthionine containing bacteriocins against certain gram negative bacteria when used in combination with chelating agents and/or surfactants or alone when used in high concentrations. Lysozyme has been shown to affect most bacteria either alone or in combination with other agents. A variety of substances have been proposed for use in combination with lysozyme. These include chelating agents such as EDTA and phytic acid, butyl P-hydroxybenzoate, P-hydroxybenzoic esters, amino acids, hydrogen peroxide and organic acids. These are reviewed by Proctor et al, supra. The synergistic combination of lysozyme with benzoic acid or sorbic acid is discussed in German patent application DE 3704-004 filed Feb. 10, 1987, and with gallic acid, phytic acid or betaine and etapoly:lysine in Japanese patent application J6 3109762, filed on Oct. 28, 1986. A bacteriocidal composition containing glucose oxidase, peroxidase, thiocyanate and lysozyme has been proposed in PCT application WO88/102600, published Apr. 21, 1988. Knorr et al report using lysozyme for the lysis of yeast (J. Food Sci., 1979, 44:1362).

The mechanism of action of lantibiotics such as nisin has not been resolved, but many investigators have linked the lethality of these peptides to irreversible changes in the cell membranes of susceptible organisms. The resistance of most organisms to nisin is thought to be due to the lack of access of the peptide to its site of action, either because of physical exclusion or the lack of appropriate receptor molecules.

The mechanism of cell lysis by n-acetylhexosaminodases such as egg-white lysozyme involves the hydrolyric cleavage of the structural component of the cell wall; in the case of bacteria, the n-acetylmuramic acid-n-acetyl glucosamine polymer, and in the case of fungi, the chitin (a n-acetyl glucosamine polymer). The synergism of lantibiotics and lysozyme may be a result of each component making the other's substrate more accessible. By degrading the structural component of microbial cell walls lysozyme may increase the accessibility of the lantibiotics to the sensitive cell membranes or particular receptor molecules which are otherwise buried beneath the cell surface.

Among the problematical gram positive bacteria, *L. monocytogenes* is a particular pest because of its ability to grow at refrigerator temperatures and its pathologic nature which can result in serious consequences when ingested. *L. monocytogenes* has been implicated in several fatalities in recent years, especially following outbreaks of listerosis associated with milk, cole slaw and soft-ripened cheese. The United States Center for Disease Control has estimated that over 1600 cases of listeriosis will occur in the U.S. annually resulting in over 400 deaths. Mothers, unborn children, newly born infants and immune compromised individuals are especially at risk. *L. monocytogenes* infections can lead to meningitis or septicemia with about 30% of diagnosed cases being fatal. Exemplary of other procaryotic microorganisms which can be controlled by the method of the present invention are gram negative bacteria such as *Salmonella typhimurium, S. enteriditis*, Shigella species, Pseudomonas species and *Escherichia coli* as well as gram positive bacteria such as species of the genera Lysteria, Clostridium, Bacillus, Staphlococcus, Streptococcus and Micrococcus.

The present invention is predicated on the discovery that a lantibiotic and lysozyme, in combination, inhibit the growth of undesirable procaryotic microorganisms to a greater degree than either material by itself and that the combined inhibitory effect of these substances is greater than the additive effect observed when using the lantibiotic or lysozyme individually. In many instances, the combination is lethal to the target organism. When using nisin as an anti-microbial agent a loading level of from 200 to 300 International Units (IU) per gram or greater of the substrate being treated is usually recommended to achieve maximal effect. Similarly, pure lysozyme is typically employed at a loading of from 20 to 100 micrograms or more per gram of the material being treated. While each of these materials by itself may be effective at these high loadings, such levels are not economically viable for many applications. The discovery that lantibiotics (such as nisin) and lysozyme in combination react in a synergistic way to inhibit the growth of bacteria facilitates the use of these materials for inhibiting bacterial contamination with greater efficacy and economy than either material by itself.

In a typical example, a substrate to be rendered resistant to undesirable microbial growth should preferably contain both a lantibiotic such as nisin and lysozyme. The total amount of nisin will typically range from about 25 IU/ml (or IU/gm in solid systems) of the material being treated up to as much as 2000 IU/ml. In most applications a nisin concentration of from 100 to 500 IU/ml will be sufficient. The ratio of nisin:lysozyme (IU/ml: μg/ml) will range from 9:1 to 1:2 with a ratio of about 2:1 being preferred. Other lantibiotics are expected to be efficacious at these concentrations although some routine experimentation may be necessary to determine the concentration of a particular lantibiotic for optimal synergistic effect. The concentrations in solid substrates would be the same except they would be converted from a volume to weight basis. Surface treatment can be accomplished by suspending and storing a material to be treated in the nisin/lysozyme solution. Alternatively, the material may be dipped in the solution or it can be sprayed onto the surface of the material. The nisin/lysozyme combination can be incorporated into films or gels which are applied to the substrate's surface or the combination can be incorporated directly into the environment being treated such as by adding it to milk to be used in making cheese. In film coating applications such as dips, films, gels or casings, the initial concentrations of the lantibiotic and lysozyme can approach their solubility limits to provide a finished product which after application and diffusion contains residual levels of lantibiotic/lysozyme which are within the proscribed limits. When treating the material's surface some routine experimentation may be needed to ascertain the most effective concentrations of lantibiotic/lysozyme.

The lactic acid bacteria, and in particular *Lactococcus lactis*, are used in the production of fermented food products such as cheese. Since some strains of *L. lactis* produce nisin, it has been suggested that these organisms be intentionally added in some fermentations so that nisin is distributed throughout the fermented food product. A major concern with this approach is that the nisin concentrations achieved may vary or be too low to be effective. However, by adding lysozyme and a small amount of additional nisin or other lantibiotic to the fermenting product, in accordance with the present invention, the amount of lantibiotic needed for effective control is reduced so that the antimicrobial effect of even low concentrations of nisin is realized.

The present invention is further illustrated by the following examples.

EXAMPLE I

Synergistic Effect of Lysozyme and Nisin on the Inhibition of Growth of *Listeria monocytogenes*

A culture of *Listeria monocytogenes* Scott A was grown overnight in Brain Heart Infusion broth (BHI, Difco Laboratories, Inc.). Overlay plates were prepared using 25 ml of BHI agar overlayed with 4 ml BHI agar containing 10 μl of the overnight culture. Sterile antibiotic sensitivity disks were blotted with 10 μl of nisin, lysozyme or nisin/lysozyme blends at various concentrations; placed on the surface of the overlay plates and incubated overnight at 37° C.

No inhibition of bacterial growth was observed with nisin at concentrations below 50 IU/ml nor was inhibition observed with lysozyme at concentrations up to and including 125 μg/ml. When a solution with 50 IU/ml nisin and 50 μg/ml lysozyme was used, however, a clear and obvious zone of inhibition was observed around the discs. Since the concentrations of nisin and lysozyme at the outer edge of the zone of inhibition must have been much less than that originally applied to the disk, one can conclude that small quantities of nisin and lysozyme act synergistically to inhibit the growth of *Listeria monocytogenes. Scott A*.

EXAMPLE II

Synergistic Effect of Lysozyme and Nisin on the Lysis of *Listeria monocytogenes*

A culture of *Listeria monocytogenes*, Scott A, was grown overnight in BHI broth and harvested by centrifugation. The harvested cells were washed with 0.067M Potassium phosphate buffer (pH 6.6) and resuspended in 0.067M potassium phosphate buffer at various pH levels to a final absorbance of about 1.0 at 540 nm as determined in a Bausch & Lomb spectronic 20. Lysis of the bacteria is accompanied by a loss in absorbance at 540 nm. Nisin and lysozyme were added to these solutions to final concentrations of 100 IU/ml nisin and 10 μg/ml lysozyme and the solutions were placed in a 37° water bath whereupon the change in adsorption at 540 nm was monitored.

The results of this experiment are graphically set out in FIG. 1. No significant change was evident in a nisin or lysozyme-free control after 5 hours. Lysis of *L. monocytogenes* by nisin alone was minimal below pH 5.5 or above pH 8.3, with maximum lysis occurring between pH 7 and 8. Lysis with lysozyme alone had its maximum at pH 6.0–6.5. At pH levels above 6.5, a definite synergistic effect between lysozyme and nisin was observed with these particular concentrations of the antimicrobials. The arithmetic sum of lysis by nisin and lysozyme is set out in the graph for comparison purposes. The comparison illustrates the synergistic effect produced by the nisin/lysozyme combination.

These results illustrate the synergism of nisin and lysozyme at various pH levels, particularly at the pH levels where the individual components are not considered to have antimicrobial activity in their own right. This is important even in systems where the pH is normally kept at low levels such as in cheese. Although the pH of cheese is usually low, the outer edges of surface ripened cheese often approach neutrality due to the action of ripening organisms in the cheese. When this happens, foodborne pathogens, such as *L. monocytogenes*, can grow on the surface of the cheese wheel. Incorporation of nisin/lysozyme at the levels previously mentioned into the cheese by surface application or their addition to the cheese milk controls this microbial growth.

EXAMPLE III

Influence of Various Ratios of Nisin/Lysozyme on Lysis of *L. monocytogenes*

Figure 2:
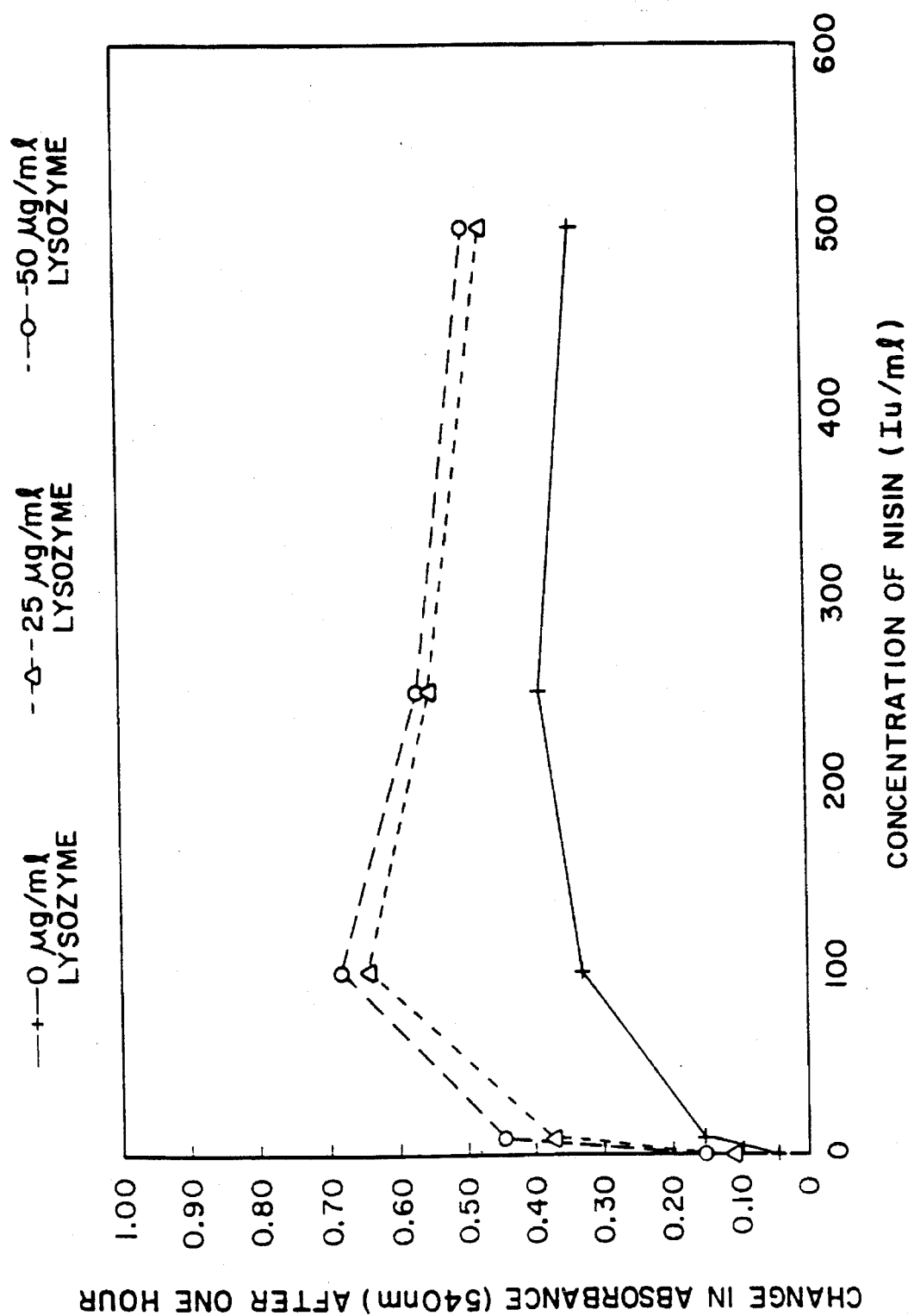
FIG. 2 is a graphical representation of lysis of *L. monocytogenes* (as expressed by change in absorbance) as a function of concentration of nisin with a constant concentration of lysozyme.

*L. monocytogenes*, Scott A strain, was grown as previously described, washed and resuspended in potassium phosphate buffer at pH 7.0. The change in absorbance after 1 hour of incubation at 37° C. of various culture preparations is set out in FIG. 2. From the data presented in this graphical representation, it can be determined that it is possible to use significantly less nisin and lysozyme in combination than either of these materials by themselves to achieve a given amount of cell lysis.

For optimal lysis of the bacteria by nisin alone, a nisin concentration of about 200 IU/ml is called for. In the case of lysozyme, concentrations in excess of 50 µg/ml (usually about 100 µg/ml) are required. It can be determined from FIG. 2 that the same rate of lysis achieved by 200 IU/ml of nisin can be achieved with about 10 IU of nisin in combination with about 25 µg/ml lysozyme. It can also be determined from FIG. 2 that the extent of lysis achieved with less than 10 IU/ml nisin and 25 µg/ml lysozyme is greater than that achieved with 200 IU/ml nisin or 50 µg/ml lysozyme used individually. This represents a potentially significant cost savings because, historically, nisin has sold for about twice the price of lysozyme. Both products are relatively expensive by food-ingredients standards causing the use of nisin at 200 IU/g or lysozyme at 100 µg/ml to be prohibitively expensive in many applications. The present invention provides a means for achieving a significant reduction in the use of nisin and lysozyme resulting in a treatment cost of only 10% of the predicted cost of using nisin alone and less than 45% of the cost occurred when lysozyme is the sole anti-microbial agent.

EXAMPLE IV

Effect of Nisin/Lysozyme on the Growth of *L. monocytogenes* in Raw Sausage

*L. monocytogenes* can grow at 5° C. and poses a threat to some processed meats. Its control can include reduction in the rate of growth, bacteriostatic effects, and most desirably, bacteriocidal effects. The synergy of the nisin/lysozyme combination was demonstrated in a complex food system (raw pork sausage) using a high level of inoculation (over $10^5$ bacteria/gram) to illustrate the utility of the present invention under worst-case conditions.

Figure 3:
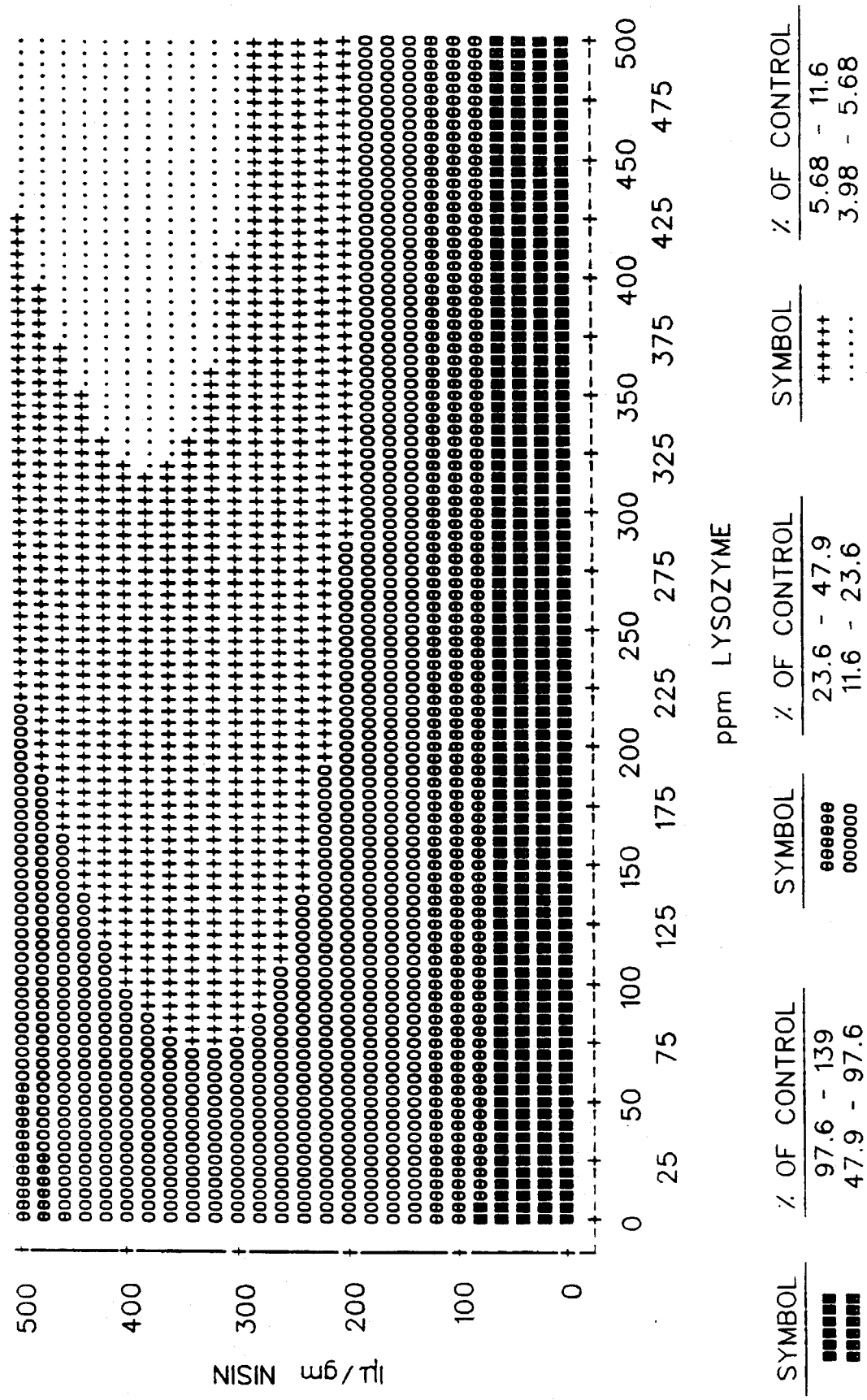
FIG. 3 is a surface response model illustrating the control of *L. monocytogenes* on raw sausage as a function of the concentration of both nisin and lysteria.

Raw sausage was inoculated with *L. monocytogenes* from a BHI overnight culture; various amounts of nisin and/or lysozyme were incorporated into the sausage. The treated sausage was held for either 3 or 21 days at 5° C. whereupon viable *L. monocytogenes* were enumerated. A surface response model was constructed over a range of 0–500 IU/gm nisin and 0–500 ppm lysozyme. The surface response model from the 3 day data are set out in the following FIG. 3. The figure demonstrates that lysozyme alone was ineffective for the control of *L. monocytogenes* in this food system, while nisin alone had some inhibitory effect. Significantly, the results show that some of the nisin can be replaced with lysozyme with the same level of control being maintained, and in some instances, significantly better performance was only achieved with the combination. For example, FIG. 3 shows that no amount of nisin or lysozyme alone was able to reduce the Listeria level to 5.68 to 11.6% of the level of the untreated control in three days, but a mixture of about 300 IU/gram nisin and 75 ppm lysozyme was able to achieve this level of control. Similar synergies are seen at other levels of nisin and lysozyme. Thus, for any desired level of control, high concentrations of nisin can be replaced by significantly lower concentrations of nisin combined with lysozyme. These results were unexpected, especially since lysozyme alone was ineffective in this food system.

EXAMPLE V

Nisin/Lysozyme Synergy Against Gram Positive Bacteria

The synergy of nisin and lysozyme is not limited to the control of *L. monocytogenes*. The minimal inhibitory concentration (MIC) of nisin was lowered by the addition of lysozyme for the control of other gram positive bacteria. For example, a culture of *Staphlococcus aureus* was grown overnight in BHI broth and subsequently diluted into fresh BHI broth with various concentrations of nisin, lysozyme or a combination of nisin and lysozyme. Lysozyme alone did not affect the subsequent growth of the bacteria at 37° C. The MIC for nisin was between 625 and 1250 IU/ml of nisin whereas the addition of a small amount of lysozyme (1 mg/ml) lowered the MIC to the 312 to 625 IU/ml range. Accordingly, one can use less nisin to provide an equivalent level of control by the addition of a synergistic amount of lysozyme.

EXAMPLE VI synergistic Effect of Lysozyme and Subtilin

A culture of *L. monocytogenes* Scott A was grown overnight in BHI broth and diluted 1:100 in 10 mM citric acid buffer (pH 5.5). This preparation, 100 µl, was added to 900 µl of citric acid buffer containing subtilin, lysozyme or both. The subtilin used in this experiment was prepared by the pure culture fermentation of *Bacillus subtillus* ATCC 6633 as described by Banerjee and Hansen in J. Biol. Chem. 1988 263 (19): 9508–9514. The results are set out in Table I.

TABLE I

| Concentration of Subtilin (IU/ml) | Concentration of Lysozyme (µg/ml) | Surviving Cells After 1 Hour at 25° C. ($\log_{10}$ colony forming units/ml) | $\log_{10}$ reduction |
|---|---|---|---|
| 0 | 0 | 7.5 | — |
| 100 µ/ml | 0 | 7.2 | 0.3 |
| 0 | 500 ppm | 7.4 | 0.1 |
| 100 µ/ml | 500 ppm | 4.9 | 2.6 |

These results show that while subtilin or lysozyme alone have little effect on the *L. monocytogenes* cells, the combination reduced the colony forming units/ml by over 99.7%. The additive effect of these antimicrobials would be expected to produce a $\log_{10}$ reduction of 0.4. The observation of a 2.6 $\log_{10}$ reduction demonstrates the synergy between this lantibiotic (subtilin) and lysozyme against *L.*

*monocytogenes.*

EXAMPLE VII

Effect of Nisin and Lysozyme on the Gram Negative Bacteria *Salmonella typhimurium*

A culture of *S. typhimurium* (ATCC 14028) was grown overnight on nutrient broth, diluted in 10 mM citric acid buffer (pH 3.5) and added to citric acid buffer containing nisin, lysozyme or a combination thereof. The results of this experiment are set out in Table II.

TABLE II

| Concentration of Nisin (IU/ml) | Concentration of Lysozyme (µg/ml) | Surviving Cells After 1 Hour at 37° C. ($\log_{10}$ colony forming units/ml) | $\log_{10}$ reduction |
|---|---|---|---|
| 0 | 0 | 7.18 | — |
| 1000 | 0 | 6.45 | 0.73 |
| 0 | 500 | 7.08 | 0.10 |
| 1000 | 500 | 5.94 | 1.24 |

These results demonstrate that lysozyme at this concentration was ineffective against *S. typhimurium* and nisin reduced the cell number by about 0.73 log units. However, use of the combination results in a reduction of 1.24 $\log_{10}$ demonstrating its synergistic activity against gram negative bacteria.

It appears that the unusual thiother linkages possessed by lantibiotics confer unique properties
upon these polypeptides which account for their antimicrobial action and the synergy with lysozyme.

What is claimed is:

1. A method for lysing *Listeria monocytogenes* in a composition containing said bacteria comprising adding to said composition a synergistically effective amount of
   a) a lantibiotic selected from the group consisting of nisin and subtilin; and
   b) lysozyme;
to effect lysis of said bacteria.

2. The method of claim 1 wherein the lysozyme is a n-acetylhexosaminodase obtained from the whites of chicken eggs.

3. The method of claim 1 wherein the lysozyme is a mucolytic enzyme obtained from human, bovine, T4 bacteriophage, bacterial, or fungal sources.

4. The method of claim 1 wherein the lantibiotic is produced by a natural or recombinant microorganism.

5. The method of claim 1 wherein the nisin is produced by pure culture fermentation of a nisin producing strain of *Lactococcus lactis*.

6. The method of claim 1 wherein the lantibiotic is present in a concentration from 25 IU/ml to 2000 IU/ml and the lantibiotic and lysozyme are present in a ratio of from 9:1 to 1:2.

7. The method of claim 6 wherein the concentration of lantibiotic is from 100 to 500 IU/ml.

8. The method of claim 1 wherein the lantibiotic and lysozyme are added to a food product to control microbial growth therein.

9. The method of claim 8 wherein the food product is selected from the group consisting of dairy products, processed meats, fresh or processed vegetables, seafood products, and beverages.

10. The method of claim 1 wherein the *L. monocytogenes* is a Scott A. strain.

11. A method of lysing *Listaria monocytogenes* in foodstuffs comprising adding to the foodstuffs a combination of a lantibiotic selected from the group consisting of nisin and subtilin and lysozyme wherein the lantibiotic is provided in an amount from 100 to 2000 IU/ml and the lantibiotic and lysozyme is present in a ratio of from 9 IU/ml:1 µg/ml to 1 IU/ml:2 µg/ml of lantibiotic:lysozyme.

12. The method of claim 11 wherein the lantibiotic is nisin.

13. The method of claim 12 wherein the nisin and lysozyme are present in a ratio of 2:1 of nisin:lysozyme.

14. The method of claim 11 wherein the lantibiotic is subtilin.

15. A method of lysing *Listaria monocytogenes* in a composition containing said bacteria which comprises adding to said composition a synergistically effective amount of a combination of about 100 IU nisin and about 10 µg/ml lysozyme while maintaining the temperature of the composition at about 37° C. and the pH at from about 6.5 to 8.5.

16. The method of claim 3 wherein the source of the lysozyme is a recombinant source.

* * * * *